(12) United States Patent
Pacetti

(10) Patent No.: US 8,349,350 B2
(45) Date of Patent: Jan. 8, 2013

(54) COATINGS FOR DRUG DELIVERY DEVICES

(75) Inventor: Stephen Dirk Pacetti, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 540 days.

(21) Appl. No.: 12/511,921

(22) Filed: Jul. 29, 2009

(65) Prior Publication Data

US 2009/0291881 A1    Nov. 26, 2009

Related U.S. Application Data

(62) Division of application No. 10/011,346, filed on Nov. 12, 2001, now Pat. No. 7,585,516.

(51) Int. Cl.
*A61F 2/06* (2006.01)
(52) U.S. Cl. ......... 424/424; 424/422; 424/425; 424/426
(58) Field of Classification Search .......... 424/489–495, 424/422–426
See application file for complete search history.

(56) References Cited

U.S. PATENT DOCUMENTS

| | | | |
|---|---|---|---|
| 3,285,897 A | 11/1966 | Sulivan et al. |
| 3,668,186 A | 6/1972 | Duncan et al. |
| 4,200,708 A | 4/1980 | McClain |
| 4,490,423 A | 12/1984 | Gould et al. |
| 4,753,652 A | 6/1988 | Langer et al. |
| 4,977,901 A | 12/1990 | Ofstead |
| 5,112,457 A | 5/1992 | Marchant |
| 5,328,471 A | 7/1994 | Slepian |
| 5,360,670 A | 11/1994 | Yonezu et al. |
| 5,455,040 A | 10/1995 | Marchant |
| 5,464,650 A | 11/1995 | Berg et al. |
| 5,534,351 A | 7/1996 | Pearson et al. |
| 5,578,073 A | 11/1996 | Haimovich et al. |
| 5,605,696 A | 2/1997 | Eury et al. |
| 5,667,767 A | 9/1997 | Greff et al. |
| 5,670,558 A | 9/1997 | Onishi et al. |
| 5,700,286 A | 12/1997 | Tartaglia et al. |
| 5,716,981 A | 2/1998 | Hunter et al. |
| 5,738,923 A | 4/1998 | Ko et al. |
| 5,824,049 A | 10/1998 | Ragheb et al. |
| 5,830,178 A | 11/1998 | Jones et al. |
| 5,837,313 A | 11/1998 | Ding et al. |
| 5,851,508 A | 12/1998 | Greff et al. |
| 5,858,746 A | 1/1999 | Hubbell et al. |
| 5,865,814 A | 2/1999 | Tuch |
| 5,873,904 A | 2/1999 | Ragheb et al. |
| 5,971,954 A | 10/1999 | Conway et al. |
| 5,980,928 A | 11/1999 | Terry |
| 5,980,972 A | 11/1999 | Ding |
| 6,013,854 A | 1/2000 | Moriuchi |
| 6,015,541 A | 1/2000 | Greff et al. |
| 6,042,875 A | 3/2000 | Ding et al. |
| 6,051,648 A | 4/2000 | Rhee et al. |
| 6,056,993 A | 5/2000 | Leidner et al. |
| 6,060,451 A | 5/2000 | DiMaio et al. |
| 6,080,488 A | 6/2000 | Hostettler et al. |
| 6,096,070 A | 8/2000 | Ragheb et al. |
| 6,096,393 A | 8/2000 | Ikeda et al. |
| 6,099,562 A | 8/2000 | Ding et al. |
| 6,110,188 A | 8/2000 | Narciso, Jr. |
| 6,113,629 A | 9/2000 | Ken |
| 6,120,536 A | 9/2000 | Ding et al. |
| 6,120,904 A | 9/2000 | Hostettler et al. |
| 6,121,027 A | 9/2000 | Clapper et al. |
| 6,129,761 A | 10/2000 | Hubbell |
| 6,153,252 A | 11/2000 | Hossainy et al. |
| 6,165,212 A | 12/2000 | Dereume et al. |
| 6,331,360 B1 | 12/2001 | Sugimoto et al. |
| 6,503,954 B1 * | 1/2003 | Bhat et al. .................. 514/772.2 |
| 2001/0014717 A1 | 8/2001 | Hossainy et al. |
| 2001/0018469 A1 | 8/2001 | Chen et al. |
| 2002/0065546 A1 * | 5/2002 | Machan et al. ............. 623/1.13 |

FOREIGN PATENT DOCUMENTS

| | | |
|---|---|---|
| EP | 0 665 023 | 8/1995 |
| EP | 0 970 711 | 1/2000 |
| WO | WO 00/12147 | 3/2000 |
| WO | WO 00/64506 | 11/2000 |
| WO | WO 01/01890 | 1/2001 |
| WO | WO 01/74414 | 10/2001 |

OTHER PUBLICATIONS

High gas-barrier resin Soarnol: Water Absorption of Soarnol (EVOH), 1998-2007; http://www.soarnol.com/eng/s_data/s_data14.html.*
Billmeyer, Texbook of Polymer Sci. 3$^{rd}$ Ed., pp. 391-395, Wiley (1984).
www.sigmaaldrich.com, Product No. 42,663-6, Poly(ethylene-co-methacrylic acid), printed May 22, 2002.
www.sigmaaldrich.com, Product No. 42,662-8, Poly(ethylene-co-methacrylic acid), printed May 22, 2002.
www.sibmaaldrich.com, Product No. 42,664-4, Poly(ethylene-co-methacrylic acid), printed May 22, 2002.
www.packagingdigest.com, Globalization of Packaging, Then and Now, Dec. 1999, pp. 48-55, printed May 22, 2002.

* cited by examiner

*Primary Examiner* — Michael G Hartley
*Assistant Examiner* — Micah-Paul Young
(74) *Attorney, Agent, or Firm* — Squire Sanders (US) LLP

(57) ABSTRACT

A polymer coating for medical devices based on a polyolefin derivative. A variety of polymers are described to make coatings for medical devices, particularly, for drug delivery stents. The polymers include homo-, co-, and terpolymers having at least one olefin-derived unit and at least one unit derived from vinyl alcohol, allyl alcohol and derivatives thereof.

14 Claims, No Drawings

COATINGS FOR DRUG DELIVERY DEVICES

This is a divisional application of U.S. application Ser. No. 10/011,346, filed on Nov. 12, 2001 now U.S. Pat. No. 7,585,516, the teaching of which is incorporated herein by reference in its entirety.

BACKGROUND OF THE INVENTION

1. Field of the Invention

This invention relates to a field of medical devices, especially the devices used for delivery of drugs. More particularly, it is directed to coatings for drug delivery devices, such as, for instance, drug eluting vascular stents.

2. Description of Related Art

In the field of medical technology, there is frequently a necessity to administer drugs locally. To provide an efficacious concentration to the treatment site, systemic administration of such medication often produces adverse or toxic side effect for the patient. Local delivery is a preferred method in that smaller total levels of medication are administered in comparison to systemic dosages, but are concentrated at a specific site. Thus, local delivery produces fewer side effects and achieves more effective results.

One commonly applied technique for local delivery of the drug is through the use of medicated stents. One method of medicating a stent is with the use of a polymer coating impregnated with the drug.

References describe a variety of polymers which can be used to coat stents. Of particular interest is a copolymer of ethylene and vinyl alcohol, also known as poly(ethylene-co-vinyl alcohol) or EVOH. Poly(ethylene-co-vinyl alcohol) is also known under the trade name EVAL and is distributed commercially by Aldrich Chemical Company of Milwaukee, Wis. EVAL is also manufactured by EVAL Company of America of Lisle, Ill.

EVAL is a product of hydrolysis of ethylene-vinyl acetate copolymers. Those having ordinary skill in the art of polymer chemistry will understand that EVAL may also be a terpolymer and may include up to 5% (molar) of units derived from styrene, propylene and other suitable unsaturated monomers. EVAL possesses a desirable impermeability to oxygen, bio- and blood-compatibility. EVAL is at least somewhat hydrophobic and thus is somewhat insensitive to moisture.

While EVAL has been shown to be a very inert and biocompatible polymer which is quite suitable for use with medical vascular devices, some of its properties can be improved. In particular, EVAL, due to a high concentration of hydroxyl groups in the vinyl component-derived units of the macromolecule, has strong interchain hydrogen bonding, which makes the polymer initially hard to dissolve in an organic solvent.

Accordingly, EVAL's solubility in organic solvents is limited. At the same time, these hydroxyl groups are responsible for insufficient water resistance, and in many applications EVAL does absorb more water than desired.

EVAL also has a high degree of crystallinity, due to the presence of the units of the macromolecule derived from the ethylene component, and a limited ability to fully control the release of drugs. EVAL's limited ability to fully control the release rate of some drugs below a certain molecular size stems from an insufficient degree of hydrophobicity of EVAL. This leads to a level of water absorption that causes the polymer to swell, increasing the polymer's porosity, and the diffusivity of the drug.

An improvement over EVAL is desired, so that the polymer forming the stent coating has a higher degree of hydrophobicity and a lower degree of crystallinity as compared to EVAL.

In view of the foregoing, it is very desirable to have alternative polymeric materials suitable for the use with various medical devices, particularly, with stents for controlled drug delivery. These polymeric materials should be bio- and blood-compatible, at least partially impermeable to oxygen, melt-processable, have reduced crystallinity, high hydrophobicity, high tensile strength and flexibility, ability to provide slower drug release rates, and be soluble in organic solvents.

The present invention provides a number of such polymers according to the following description.

SUMMARY

The embodiments of this invention provide a number of polymers to be used in coatings with medical devices, particularly, with stents for controlled local delivery of drugs. The drugs to be delivered are generally incorporated into the coatings.

The polymers used in the embodiments of this invention can be divided into several categories. The first category includes copolymers of an olefin, typically, ethylene (but also propylene) with a vinyl component containing a hydroxymethyl group. These vinyl components are derivatives of allyl alcohol. Examples of the polymers in this category include poly(ethylene-co-allyl alcohol), a terpolymer poly(ethylene-co-allyl alcohol-co-vinyl alcohol), poly(propylene-co-allyl alcohol), poly(ethylene-co-methallyl alcohol), a terpolymer poly(propylene-co-allyl alcohol-co-vinyl alcohol), and poly(propylene-co-methallyl alcohol).

The second category includes polymers having units derived from vinyl alcohol, but no units derived from allyl alcohol. This group includes poly(propylene-co-vinyl alcohol), poly(ethylene-co-methvinyl alcohol), poly(propylene-co-methvinyl alcohol), and a terpolymer poly(propylene-co-ethylene-co-vinyl alcohol).

Finally, the third category includes a homopolymer polyallyl alcohol.

In addition, the embodiments of this invention provide for a number of coatings fabricated from a variety of terpolymers. The terpolymers are obtained by co-polymerization of an olefin component with a hydroxyl-containing component. These terpolymers are discussed in detail below.

When a coating is made out of one of the polymers described above, a drug to be delivered in a localized fashion is incorporated into the coating. Examples of the drugs include antiproliferative substances such as actinomycin D, or derivatives and analogs thereof.

The active agent can also fall under the genus of antineoplastic, anti-inflammatory, antiplatelet, anticoagulant, antifibrin, antithrombin, antimitotic, antibiotic, antiallergic and/or antioxidant substances. Particular examples of these and other usable drugs and active agents are provided below.

The drug is typically incorporated into a coating matrix on a drug delivery stent, the coating made out of one of the polymers provided in the embodiments of this invention. In addition, the coatings can be used on the stent as a primer, rate release limiting membrane, and/or biocompatible topcoat.

According to one aspect of this invention, a coating for medical devices is provided, the coating comprising a polymer having a formula $-[CH_2-CHR^1]_m[CH_2-CR^2(CH_2OH)]_n-[CH_2-CH(OH)_x]_o$, wherein $R^1$ and $R^2$ is each selected, independently, from a group consisting of hydrogen and an alkyl group; m and n is each, independently, an integer within a range of between about 30 and about 7,600; o is an integer within a range of between 0 and about 7,600; and x equals 1 if o equals at least 1. When $R^1$ or $R^2$ or both is an alkyl group, the alkyl group is typically, but not necessarily, a methyl group.

According to another aspect of this invention, a coating for medical devices is provided, the coating comprising a polymer having a formula $—[CH_2—CH(CH_3)]_p—[CH_2—CR^3(OH)]_q—[CH_2—CH(CH_2OH)_y]_r—$, wherein $R^3$ is selected from a group consisting of hydrogen, and an alkyl group; p and q is each, independently, an integer within a range of between about 30 and about 7,600; r is an integer within a range of between 0 and about 7,600; and y equals 1 if r equals at least 1. As in the previous aspect of this invention, when $R^3$ is an alkyl group, the alkyl group is typically, but not necessarily, a methyl group.

According to yet another aspect of this invention, a coating for medical devices is provided, the coating comprising a polymer selected from a group consisting of poly(ethylene-co-α-methvinyl alcohol), poly(propylene-co-ethylene-co-vinyl alcohol), and polyallyl alcohol.

According to another aspect of this invention, a coating for medical devices is provided, the coating comprising a polymer, the polymer being a terpolymer comprising one or more units derived from an olefin and one or more units derived from an unsaturated hydroxylated monomer.

According to another aspect of this invention, a polymer coating for medical devices is provided, the coating comprising a polyolefin derivative.

According to yet another aspect of this invention, a polymeric film-former for coatings for medical devices is provided, the polymer comprising a polyolefin.

DETAILED DESCRIPTION

A family of polymers used to make coatings for medical devices, in particular, for drug delivery stent, is characterized by the presence of a polyolefin backbone, pendant on which are alkyl, hydroxyl, and/or hydroxyalkyl groups.

It is known, that while EVAL has good oxygen-barrier properties and some resistance to water vapor, as well as good biocompatibility, its solubility in organic solvents and its ability to provide slow drug release are limited. These drawbacks are caused by the strong hydrogen bonding between the hydroxyl groups, which makes the polymer initially hard to dissolve in a solvent, but which also leads to swelling of the polymer in water.

All polymers disclosed below are somewhat related to EVAL, but have better properties for the purposes of making coatings for medical devices. Particularly, they possess a higher degree of hydrophobicity and lower degree of crystallinity as compared to EVAL.

The reason for such improved properties is that, compared with EVAL, the polymers can be more hydrophobic, lowering the degree of water swelling. The polymers can also be more readily dissolved in organic solvents by having less hydrogen bonding, due to a lower hydroxyl content, and less crystallinity.

Improved hydrophobicity of these polymers lowers the equilibrium water absorption, allowing slower drug release than what is possible for of EVAL.

For a polymer to be useful in a coating for a drug delivery device, it should satisfy at least the following requirements. It should absorb not more than about 5% of water (by weight). It should have an ultimate tensile strength of at least 3,500 psi (about 24.2 MPa), and, at the same time, an ultimate elongation to failure exceeding 30%. It should be soluble in at least some organic solvents even if those as strong as dimethylsulfoxide (DMSO) are required. Generally, it should be possible to make at least a 2% (by weight) solution of the polymer in a solvent, such as DMSO, DMAC, DMF, methanol, toluene, isopropyl alcohol, trifluoroethanol, hexafluoroisopropanol, and similar solvents.

All the polymers, copolymers and terpolymers according to the embodiments of this invention described below satisfy these criteria.

The following examples show the polymers, copolymers, and terpolymers used to make coatings for medical devices of the present invention.

Example 1

Poly(ethylene-co-allyl Alcohol)

This polymer has the formula: $—[CH_2—CH_2]_m—[CH_2—CH(CH_2OH)]_n—$.

The polymer is synthesized by free radical co-polymerization of ethylene and methyl acrylate followed by treatment of the resulting poly(ethylene-co-methyl acrylate) with a strong reducing agent, for instance, a metal hydride. As a result of the reaction of reduction, the hydroxymethyl group of allyl alcohol is formed.

The polymer can also be synthesized by polymerization of ethylene with acrylic acid followed by reduction. Free radical polymerization of allyl acetate with ethylene followed by base hydrolysis results in the same polymer. This last reaction scheme has the advantage of not using costly metal hydride reagents. The process of free radical polymerization, metal hydride reduction, and base hydrolysis mentioned above are known to those having ordinary skill in the art.

The resulting polymer, poly(ethylene-co-allyl alcohol), is more hydrophobic and thus more soluble in organic solvents than EVAL and it can be used to form coatings on medical devices.

Example 2

Poly(ethylene-co-allyl alcohol-co-vinyl Alcohol)

The polymer has the following formula: $—[CH_2—CH_2]_m—[CH_2—CH(CH_2OH)]_n—[CH_2—CH(OH)]_o—$. This terpolymer can be synthesized from several different sets of starting monomers. Ethylene, methyl acrylate and vinyl acetate can be copolymerized by free radical initiators, followed by reduction with a strong reducing agent, such as a metal hydride, for instance, lithium aluminum hydride (LiAlH$_4$). Similarly, ethylene, allyl acetate, and vinyl acetate could be polymerized and reduced to yield the same product.

Alternatively, ethylene, allyl acetate, and vinyl acetate could be copolymerized and the alcohol groups then formed by catalytic base hydrolysis of the acetate moieties. Lastly, the free radical polymerization product of ethylene, methylacrylate and vinyl acetate can first be base hydrolyzed to the corresponding alcohol and carboxyl groups. Hydride reduction of the carboxyl group completes the synthesis and requires less hydride reagent than that required in the first reaction scheme.

Example 3

Poly(propylene-co-vinyl Alcohol)

The polymer has the formula $—[CH_2—CH(CH_3)]_m—[CH_2—CH(OH)]_n—$. This polymer is synthesized in a way similar to the synthesis of EVAL, except instead of ethylene, propylene is copolymerized in the usual fashion, by a free radical process with vinyl acetate, followed by hydrolysis of the acetate groups of the resulting copolymer. The process is understood by those having ordinary skill in the art. The final product is very likely to be atactic, with a crystallinity adjustable by varying the monomer ratios, and thus has a higher solubility in organic solvents than EVAL.

Example 4

Poly(propylene-co-allyl Alcohol)

The polymer has the formula $-[CH_2-CH(CH_3)]_m-[CH_2-CH(CH_2OH)]_n-$. This polymer is synthesized in a way similar to the synthesis of poly(ethylene-co-allyl alcohol) described in the Example 1, above, only here a poly(propylene-co-methyl acrylate) precursor is used instead of poly(ethylene-co-methyl acrylate) precursor of the Example 1.

Example 5

Poly(propylene-co-allyl alcohol-co-vinyl Alcohol)

The polymer has the formula: $-[CH_2-CH(CH_3)]_m-[CH_2-CH(OH)]_n-[CH_2-CH(CH_2OH)]_o-$.

This terpolymer is synthesized in a manner similar to what is described in Example 2, above. Of course, instead of ethylene, propylene is used here at the stage of copolymerization.

Example 6

Poly(ethylene-co-methallyl Alcohol)

The polymer has the formula $-[CH_2-CH_2]_m-[CH_2-C(CH_3)(CH_2OH)]_n-$. The precursor used to fabricate this polymer is the copolymer of ethylene and methacrylic acid. The synthesis of this polymer is achieved by reduction of the carboxyl group of the precursor to the hydroxyl group. A second synthetic pathway would be co-polymerization of ethylene and methyl methacrylate followed by reduction.

Example 7

Poly(propylene-co-methallyl Alcohol)

The polymer has the formula $-[CH_2-CH(CH_3)]_m-[CH_2-C(CH_3)(CH_2OH)]_n-$. It is synthesized in a manner similar to the synthesis of poly(ethylene-co-methallyl alcohol), described in Example 6, above, except instead of the poly(ethylene-co-methacrylic acid) precursor used in Example 6, a poly(propylene-co-methacrylic acid) precursor is used.

Example 8

Poly(ethylene-co-methyinyl Alcohol)

The polymer has the formula $-[CH_2-CH_2]_m-[CH_2-C(CH_3)(OH)]_n-$. This polymer has a structure very similar to that of EVAL, the only difference being that the carbon in EVAL which bears the hydroxyl group is also substituted with a methyl group. Consequently, the properties of this copolymer are similar to those of EVAL. However, it can be beneficially distinguished from EVAL in that its solubility in organic solvents, due to the presence of an extra methyl group, is better that the solubility of EVAL.

This copolymer can be synthesized by saponification of the acetate groups of a poly(ethylene-co-methyinyl acetate) (also known as poly(ethylene-co-isopropenyl acetate)) precursor. The preparation of this precursor as well as the saponification are conducted in a common manner known to those skilled in the art.

Example 9

Poly(propylene-co-methyinyl Alcohol)

The polymer has the formula $-[CH_2-CH(CH_3)]_m-[CH_2-C(CH_3)(OH)]_n-$. This polymer is anticipated to have an amorphous structure due to the presence of atactic propylene groups. Its synthesis is analogous to that of poly(ethylene-co-methyinyl alcohol) described in Example 8, above. The synthesis here involves the saponification of the acetate groups of a poly(propylene-co-methvinyl acetate) precursor according to usual methods known to persons having ordinary skill in the art of polymer chemistry.

Example 10

Poly(propylene-co-ethylene-co-vinyl Alcohol)

The polymer has the formula: $-[CH_2-CH(CH_3)]_m-[CH_2-CH_2]_n-[CH_2-CH(OH)]_o-$. This terpolymer made by substituting some of the ethylene in the current synthesis of EVAL with propylene. This leads to lower crystallinity and increased hydrophobicity of this polymer as compared to EVAL, while retaining all beneficial properties of EVAL.

Example 11

Polyallyl Alcohol

This homopolymer has the formula $-[CH_2-CH(CH_2OH)]_m-$. It can be synthesized in any common way known to those having ordinary skill in the art, including free radical polymerization of allyl alcohol. However, polyallyl alcohol is not easily synthesized from allyl alcohol to high molecular weight by conventional free radical polymerization techniques due to degradative chain transfer reactions.

One technique disclosed in the U.S. Pat. No. 3,285,897 to Sullivan, et. al. utilizes polymerization at high pressure in the presence of a free radical polymerization catalyst. U.S. Pat. No. 6,096,393 to Ikeda, et. al. discloses several synthetic pathways including free radical polymerization of methacrylic acid or methyl methacrylate followed by reduction with a metal hydride.

Polyallyl alcohol is hydrophobic and not soluble in water, but is soluble in some rather strong organic solvents, such as dioxane, tetrahydrofuran, or methanol. Its oxygen barrier properties are excellent.

In general, for any polymer, copolymer, or terpolymer discussed in Examples 1-11 above, as the content of the olefinic moiety in the polymer, copolymer, or terpolymer increases, its elongation to failure also increases, while both its capacity to absorb water and its ultimate tensile strength decrease.

In order to achieve the desired water absorption as well as desired mechanical properties (ultimate tensile strength, elongation to failure) and solubility, the ratio of monomers is adjusted to yield a polymer having the properties in the desired range. Accordingly, the ratios for the monomers used to obtain polymers, copolymers, and terpolymers of Examples 1-11 should be within a range as shown in Table 1.

TABLE 1

Compositions of (Co)polymers of Examples 1-11.

| Example No. | Monomer 1 | Monomer 2 | Monomer 3 | Total |
|---|---|---|---|---|
| 1 | Ethylene $m = 30\text{-}7,600$ | Allyl Alcohol $n = 30\text{-}7,600$ | None | $m + n ==$ $300\text{-}8,400$ |
| 2 | Ethylene $m = 30\text{-}7,600$ | Allyl Alcohol $n = 30\text{-}7,600$ | Vinyl Alcohol $o = 30\text{-}7,600$ | $m + n + o ==$ $600\text{-}4,200$ |
| 3 | Propylene $m = 30\text{-}7,600$ | Vinyl Alcohol $n = 30\text{-}7,600$ | None | $m + n ==$ $300\text{-}8,400$ |
| 4 | Propylene $m = 30\text{-}7,600$ | Allyl Alcohol $n = 30\text{-}7,600$ | None | $m + n ==$ $300\text{-}8,400$ |
| 5 | Propylene $m = 30\text{-}7,600$ | Allyl Alcohol $n = 30\text{-}7,600$ | Vinyl Alcohol $o = 30\text{-}7,600$ | $m + n + o ==$ $300\text{-}8,400$ |
| 6 | Ethylene $m = 30\text{-}7,600$ | Methallyl Alcohol $n = 30\text{-}7,600$ | None | $m + n ==$ $300\text{-}8,400$ |
| 7 | Propylene $m = 30\text{-}7,600$ | Methallyl Alcohol $n = 30\text{-}7,600$ | None | $m + n ==$ $300\text{-}8,400$ |
| 8 | Ethylene $m = 30\text{-}7,600$ | Methvinyl Alcohol $n = 30\text{-}7,600$ | None | $m + n ==$ $300\text{-}8,400$ |
| 9 | Propylene $m = 30\text{-}7,600$ | Methvinyl Alcohol $n = 30\text{-}7,600$ | None | $m + n ==$ $300\text{-}8,400$ |
| 10 | Propylene $m = 30\text{-}7,600$ | Ethylene $n = 30\text{-}7,600$ | Vinyl Alcohol $o = 60\text{-}3,800$ | $m + n + o ==$ $300\text{-}8,400$ |
| 11 | Allyl alcohol | None | None | $n = 30\text{-}7,600$ |

In addition to the above-discussed eleven examples describing embodiments of this invention, there exist a large number of polymers that can be also used to make coatings for medical instruments, particularly, for controlled drug delivery stents.

Such polymers comprise products of copolymerization of an olefin co-monomer component and a hydroxylated monounsaturated co-monomer component. Typically, one of the olefin components is mixed and co-polymerized with any two of the hydroxylated components, or vice versa, one of the hydroxylated components is mixed and co-polymerized with any two of the olefin components.

The process of co-polymerization usually involves a free radical co-polymerization, but any other otherwise acceptable method of co-polymerization known to those skilled in the art can be used as well. A large number of terpolymers is, thus, available as a result.

Examples of an olefin component comprise ethylene, propylene, and any butene. Generally, any olefin, straight-chained or branched, having between two and eight carbons can be used. Using olefins with larger number of carbon atoms is not advisable because polymerization will be difficult since the reactivity of such olefins will be decreased due to their increased bulkiness and an increase in steric hindrance.

Examples of a hydroxylated monounsaturated component include vinyl alcohol and its derivatives (i.e., methvinyl alcohol and the like), allyl alcohol and its derivatives (i.e., methallyl alcohol and the like), 1-hydroxy-2-methyl ethylene, 1-hydroxy-2-methyl propene, and a number of butene-ols (i.e., 3-butene-1-ol, 3-butene-2-ol, 3-butene-3-ol, 3-butene-4-ol and 2-butene-1-ol).

Obviously, by matching various combinations of olefinic components with hydroxylated monounsaturated components, a very large number of terpolymers may be obtained. The longer and the bulkier the groups on the polymer backbone, the less is the polymer's tendency to crystallize. This is a positive feature of such bulkier macromolecules, because their ability to dissolve in organic solvents is increased.

It should be also borne in mind, than every time a vinyl alcohol group is present, it was either created by saponification or reduction of an acetate moiety. Therefore, the polymers having the acetate group only partially converted to hydroxyl functionality are also included in the list of the embodiments discussed above. Obviously, such polymers will have both acetate and vinyl alcohol groups. In addition to the products having vinyl alcohol groups, some other above-mentioned terpolymers are also obtained by saponification of the acetate moieties. Such terpolymers include those based on 3-butene-3-ol, 3-butene-4-ol, and 1-hydroxy-2-methyl-propene.

A polymer of this invention is used on a medical device, particularly, on a drug delivery stent. The invention is used as a coating matrix on the stent. The coating polymer can have several functions. The coating can be used as a primer, as a matrix carrying the drug, as a rate release limiting membrane and/or as a bio- and/or blood-compatible topcoat.

In any of these cases, the coating is applied onto the stent by a commonly used method known to the practitioners of the art, for instance, by spraying, dipping or molding, as described in Examples 12 and 13, below. The drug can be incorporated within the coating, or the drug can be in a separate layer underneath the coating, or the drug can be adsorbed onto the surface of the coating.

Example 12

Poly(ethylene-co-allyl alcohol) Based Coating

Poly(ethylene-co-allyl alcohol), the polymer of Example 1 above, is synthesized with a monomer ratio (by moles) of about 1:1. The molecular weight of ethylene is 28 and of allyl alcohol—58, and both "m" and "n" are equal to a value of about 870. A number average molecular weight of the polymer is about 75,000. The polymer is dissolved in a mixture of solvents comprising 50% of DMSO and 50% of DMAC (by weight) to form a 2% solution (by weight).

A spray apparatus, such as an EFD 780S spray nozzle with a VALVEMATE 7040 control system, manufactured by EFD, Inc. of East Providence, R.I. is used to apply the polymer solution to a stent. The EFD 780S spray nozzle is an air-assisted external mixing atomizer. The composition is atomized by air and applied to the stent surfaces. During the process of applying the composition, the stent can be optionally rotated about its longitudinal axis, at a speed of 50 to about 150 rpm. The stent can also be linearly moved along the same axis during the application.

The 2% solution of the polymer is applied to a 13-mm TETRA stent (available from Guidant Corporation) in a series of 10-second passes, to deposit 10 μg of coating per spray pass. Between the spray passes, the stent is dried for 10 seconds using flowing air with a temperature of 60° C. Five spray passes are applied to form a 50 μg primer layer, followed by baking the primer layer at 140° C. for one hour.

A drug containing formulation is prepared comprising 2% of the polymer, 0.66% of actinomycin D and 97.34% of a mixture of solvents comprising 50% of DMSO and 50% of DMAC. All percentage amounts are by weight. In a manner identical to the application of the primer layer, five spray passes are performed to form a 50 μg drug-polymer layer, followed by baking the drug-polymer layer at 50° C. for 2 hours.

Finally, a topcoat composition to control the drug release rate is prepared, comprising 2% of the polymer and 98% of a mixture of solvents comprising 50% of DMAC, 20% of DMSO and 30% of ethanol. All percentage amounts are by weight. In a manner identical to the application of the primer layer and the drug-polymer layer, thirty-five spray passes are performed to form a 350 μg topcoat layer, followed by final baking at 50° C. for 2 hours.

Example 13

Poly(propylene-co-vinyl alcohol) Based Coating

Poly(propylene-co-vinyl alcohol), the polymer of Example 3 above, is synthesized with a monomer ratio of the propylene segments and the vinyl alcohol segments (by moles) of about 44:56. The molecular weight of propylene is 42 and of vinyl alcohol 44. The value for "m" in the polymer is about 765, and for "n"—about 974. A number average molecular weight of the polymer is about 75,000. The free radical polymerization results in the propylene component being atactic. The polymer is dissolved in DMAC to form a 2% solution (by weight).

Using the process and equipment described in Example 12, above, the 2% solution of the polymer is applied to a 13-mm TETRA stent. Five spray passes are applied to form a 50 μg primer layer, followed by baking the primer layer at 140° C. for one hour.

A drug containing formulation is prepared comprising 2% of the polymer, 1% of β-estradiol and 97% of DMAC. All percentage amounts are by weight. In a manner identical to the application of the primer layer, thirty spray passes are performed to form a 300 μg drug-polymer layer, followed by baking the drug-polymer layer at 50° C. for 2 hours.

Finally, a topcoat composition to control the drug release rate is prepared, comprising 2% of the polymer and 98% of a mixture of solvents comprising 70% of DMAC and 30% of ethanol. All percentage amounts are by weight. In a manner identical to the application of the primer layer and the drug-polymer layer, thirty spray passes are performed to form a 300 μg topcoat layer, followed by final baking at 50° C. for 2 hours.

The stent, or other implantable medical device can be used in any part of the vascular system, including neurological, carotid, coronary, renal, aortic, iliac, femoral or any other peripheral vascular lumens. The are no limitations on the size of the implantable medical device, its length, diameter, strut thickness or pattern. Examples of such implantable devices include self-expandable stents, balloon-expandable stents, stent-grafts, grafts (e.g., aortic grafts), artificial heart valves, cerebrospinal fluid shunts, coronary shunts, pacemaker electrodes, and endocardial leads (e.g., FINELINE and ENDOTAK, available from Guidant Corporation). The underlying structure of the device can be of virtually any design. The device can be made of a metallic material or an alloy such as, but not limited to, cobalt chromium alloy (EL-GILOY), stainless steel (316L), "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention.

There no limitations on the drugs to be incorporated within the coating. For example, the active agent of the drug could be designed to inhibit the activity of vascular smooth muscle cells. It can be directed at inhibiting abnormal or inappropriate migration and/or proliferation of smooth muscle cells to inhibit restenosis.

Generally speaking, the drug can include any substance capable of exerting a therapeutic or prophylactic effect in the practice of the present invention. The drug may include small molecule drugs, peptides, proteins, oligonucleotides, or double-stranded DNA.

Examples of the drugs which are usable include antiproliferative substances such as actinomycin D, or derivatives and analogs thereof. Synonyms of actinomycin D include dactinomycin, actinomycin IV, actinomycin $I_1$, actinomycin $X_1$, and actinomycin $C_1$.

The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel, docetaxel, methotrexate, azathioprine, vincristine, vinblastine, fluorouracil, doxorubicin hydrochloride, and mitomycin.

Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin.

Examples of such cytostatic or antiproliferative agents include angiopeptin, angiotensin converting enzyme inhibitors such as captopril, cilazapril or lisinopril, calcium channel blockers (such as nifedipine), colchicine, fibroblast growth factor (FGF) antagonists, fish oil (ω-3-fatty acid), histamine antagonists, lovastatin (an inhibitor of HMG-CoA reductase, a cholesterol lowering drug), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide.

An example of an antiallergic agent is permirolast potassium. Other therapeutic substances or agents which may be appropriate include alpha-interferon, genetically engineered epithelial cells, rapamycin and dexamethasone.

Having described the invention in connection with several embodiments thereof, modification will now suggest itself to those skilled in the art. As such, the invention is not to be limited to the described embodiments.

What is claimed is:

1. A coating for a medical device, the coating comprising a polymer having a formula:

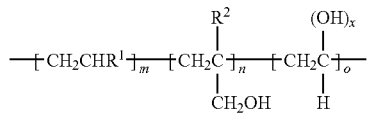

wherein $R^1$ is selected from a group consisting of a hydrogen atom and an alkyl group; and
$R^2$ is selected from a group consisting of a hydrogen atom and an alkyl group, wherein the coating contains a drug, and
m is an integer within a range of between about 30 and about 7,600;
n is an integer within a range of between about 30 and about 7,600;
o is an integer within a range of between 0 and about 7,600; and
x equals 1 if o equals at least 1.

2. The coating of claim 1, wherein the alkyl group is methyl.

3. The coating of claim 1, wherein the polymer absorbs not more than 5% of water by mass.

4. The coating of claim 1, wherein the polymer is soluble in an organic solvent.

5. The coating of claim 1, wherein the polymer has a tensile strength of not less than about 24 MPa (3,500 pounds per square inch).

6. The coating of claim 1, wherein the polymer has an ultimate elongation exceeding 30 percent.

7. A coating for a stent, the coating comprising a polymer having a formula:

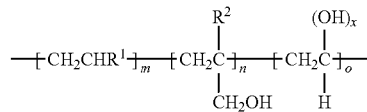

wherein $R^1$ is selected from a group consisting of a hydrogen atom and an alkyl group; and
$R^2$ is selected from a group consisting of a hydrogen atom and an alkyl group;
m is an integer within a range of between about 30 and about 7,600;
n is an integer within a range of between about 30 and about 7,600;
o is an integer within a range of between 0 and about 7,600; and
x equals 1 if o equals at least 1.

8. The coating of claim 7, wherein the coating is a primer layer.

9. The coating of claim 7, wherein the coating is a rate release limiting membrane.

10. The coating of claim 7, wherein the alkyl group is methyl.

11. The coating of claim 7, wherein the polymer absorbs not more than 5% of water by mass.

12. The coating claim 7, wherein the polymer is soluble in an organic solvent.

13. The coating of claim 7, wherein the polymer has a tensile strength of not less than about 24 MPa (3,500 pounds per square inch).

14. The coating of claim 7, wherein the polymer has an ultimate elongation exceeding 30 percent.

* * * * *